(12) United States Patent
Gainor

(10) Patent No.: US 9,931,205 B2
(45) Date of Patent: *Apr. 3, 2018

(54) LOW-PROFILE PROSTHETIC VALVE STRUCTURE

(71) Applicant: HLT, Inc., Maple Grove, MN (US)

(72) Inventor: John P. Gainor, Mendota Heights, MN (US)

(73) Assignee: HLT, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,543

(22) Filed: Oct. 7, 2016

(65) Prior Publication Data

US 2017/0020667 A1 Jan. 26, 2017

Related U.S. Application Data

(63) Continuation of application No. 14/212,442, filed on Mar. 14, 2014, now Pat. No. 9,486,314.

(60) Provisional application No. 61/800,153, filed on Mar. 15, 2013.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2427* (2013.01); *A61F 2220/0075* (2013.01); *A61F 2220/0091* (2013.01)

(58) Field of Classification Search
CPC .... A61F 2/2403; A61F 2/2427; A61F 2/2412; A61F 2/2418; A61F 2220/0091; A61F 2220/0075; A61F 2220/00832; A61F 2/2409

USPC ........................................................ 623/2.11
See application file for complete search history.

(56) References Cited

U.S. PATENT DOCUMENTS

| | | |
|---|---|---|
| 4,056,854 A | 11/1977 | Boretos et al. |
| 5,549,665 A | 8/1996 | Vesely et al. |
| 5,669,931 A | 9/1997 | Kupiecki et al. |
| 5,843,260 A | 12/1998 | Huskey |
| 5,846,261 A | 12/1998 | Kotula et al. |
| 6,015,431 A | 1/2000 | Thornton et al. |
| 6,016,810 A | 1/2000 | Ravenscroft |
| 6,126,686 A | 10/2000 | Badylak et al. |
| 6,168,614 B1 | 1/2001 | Andersen et al. |
| 6,287,335 B1 | 9/2001 | Drasler et al. |
| 6,378,028 B2 | 4/2002 | Inagawa et al. |
| 6,402,780 B2 | 6/2002 | Williamson, IV et al. |
| 6,425,916 B1 | 7/2002 | Garrison et al. |
| 6,478,028 B1 | 11/2002 | Paolitto et al. |
| 6,524,339 B1 | 2/2003 | Adams |
| 6,592,614 B2 | 7/2003 | Lenker et al. |

(Continued)

FOREIGN PATENT DOCUMENTS

| | | |
|---|---|---|
| CA | 2863503 A1 | 8/2013 |
| CN | 101991478 B | 4/2013 |

(Continued)

*Primary Examiner* — Diane Yabut
*Assistant Examiner* — Erich Herbermann
(74) *Attorney, Agent, or Firm* — Inskeep IP Group, Inc.

(57) ABSTRACT

A prosthetic valve assembly that includes a stent, a tissue sleeve and an anchoring mechanism. By loading the three components of the valve assembly into a delivery catheter in a series formation, such that no two components are located within each other, the size of the delivery catheter can be reduced.

20 Claims, 3 Drawing Sheets

(56) References Cited

U.S. PATENT DOCUMENTS

| | | |
|---|---|---|
| 6,605,102 B1 | 8/2003 | Mazzocchi et al. |
| 6,652,578 B2 | 11/2003 | Bailey et al. |
| 6,719,781 B1 | 4/2004 | Kim |
| 6,769,434 B2 | 8/2004 | Liddicoat et al. |
| 6,893,457 B2 | 5/2005 | Dong |
| 6,908,481 B2 | 6/2005 | Cribier |
| 6,929,653 B2 | 8/2005 | Strecter |
| 7,001,425 B2 | 2/2006 | McCullagh et al. |
| 7,252,681 B2 | 8/2007 | Berg et al. |
| 7,267,686 B2 | 9/2007 | Dimatteo et al. |
| 7,329,279 B2 | 2/2008 | Haug et al. |
| 7,445,630 B2 | 11/2008 | Lashinski et al. |
| 3,021,420 A1 | 9/2011 | Dolan |
| 8,157,796 B2 | 4/2012 | Collins et al. |
| 8,663,312 B2 | 3/2014 | Wilson et al. |
| 8,696,737 B2 | 4/2014 | Gainor |
| 8,845,720 B2 | 9/2014 | Conklin |
| 8,986,374 B2 | 3/2015 | Cao et al. |
| 2002/0032481 A1 | 3/2002 | Gabbay |
| 2002/0128703 A1 | 9/2002 | Ravenscroft |
| 2003/0014104 A1 | 1/2003 | Cribier |
| 2004/0024416 A1 | 2/2004 | Yodfat et al. |
| 2004/0073293 A1 | 4/2004 | Thompson |
| 2004/0073301 A1 | 4/2004 | Donlon et al. |
| 2004/0093075 A1 | 5/2004 | Kuehne |
| 2004/0220664 A1 | 11/2004 | Chobotov |
| 2004/0260333 A1 | 12/2004 | Dubrul et al. |
| 2005/0022674 A1 | 2/2005 | Campbell et al. |
| 2005/0075720 A1 | 4/2005 | Nguyen et al. |
| 2005/0137691 A1 | 6/2005 | Salahieh et al. |
| 2005/0137702 A1 | 6/2005 | Haug et al. |
| 2005/0222674 A1 | 10/2005 | Paine |
| 2005/0240200 A1 | 10/2005 | Bergheim |
| 2005/0251251 A1 | 11/2005 | Cribier |
| 2005/0283231 A1 | 12/2005 | Haug et al. |
| 2006/0020327 A1 | 1/2006 | Lashinski et al. |
| 2006/0074484 A1 | 4/2006 | Huber |
| 2006/0142848 A1 | 6/2006 | Gabbay |
| 2006/0167468 A1 | 7/2006 | Gabbay |
| 2007/0010876 A1 | 1/2007 | Salahieh et al. |
| 2007/0203517 A1 | 8/2007 | Williams et al. |
| 2008/0015671 A1 | 1/2008 | Bonhoeffer |
| 2008/0071362 A1 | 3/2008 | Tuval et al. |
| 2008/0195199 A1 | 8/2008 | Kheradvar et al. |
| 2008/0300678 A1 | 12/2008 | Eidenschink et al. |
| 2009/0076598 A1 | 3/2009 | Salahieh et al. |
| 2009/0222076 A1 | 9/2009 | Figulla et al. |
| 2010/0161028 A1* | 6/2010 | Chuter ............... A61F 2/07 623/1.13 |
| 2010/0168839 A1 | 7/2010 | Braido et al. |
| 2011/0218619 A1 | 9/2011 | Benichou et al. |
| 2011/0264206 A1 | 11/2011 | Tabor |
| 2011/0282439 A1 | 11/2011 | Thill et al. |
| 2012/0065728 A1 | 3/2012 | Gainor et al. |
| 2012/0209370 A1 | 8/2012 | Thill et al. |
| 2013/0144383 A1 | 6/2013 | Thill et al. |
| 2013/0204357 A1 | 8/2013 | Thill et al. |
| 2013/0204360 A1 | 8/2013 | Gainor |
| 2013/0282098 A1 | 10/2013 | Thill et al. |
| 2014/0155996 A1 | 6/2014 | Wilson et al. |

FOREIGN PATENT DOCUMENTS

| | | |
|---|---|---|
| DE | 102005052628 A1 | 5/2007 |
| EP | 1 915 105 A2 | 4/2008 |
| EP | 2 809 272 A1 | 12/2014 |
| EP | 2 967 861 A1 | 1/2016 |
| JP | H0611637 A | 1/1994 |
| JP | H1029161 A | 2/1998 |
| JP | 2000-291883 A | 10/2000 |
| JP | 2002-182095 A | 6/2002 |
| JP | 2002-228903 A | 8/2002 |
| JP | 2002-328317 A | 11/2002 |
| JP | 2002-537943 A | 11/2002 |
| JP | 2003-506133 A | 2/2003 |
| JP | 2003-098443 A | 4/2003 |
| JP | 2004-503327 A | 2/2004 |
| JP | 2007-237136 A | 9/2007 |
| JP | 4093401 B2 | 6/2008 |
| JP | 4549278 B2 | 9/2010 |
| JP | 5289049 B2 | 9/2013 |
| JP | 2014-000472 A | 1/2014 |
| JP | 2015-509033 A | 3/2015 |
| JP | 5749231 B2 | 7/2015 |
| JP | 2016-028783 A | 3/2016 |
| JP | 2016-064147 A | 4/2016 |
| WO | 1997/027799 A1 | 8/1997 |
| WO | 1997/030659 A1 | 8/1997 |
| WO | 1999/015112 A1 | 4/1999 |
| WO | 2000/053120 A1 | 9/2000 |
| WO | 2002/005729 A2 | 1/2002 |
| WO | 2003/092554 A1 | 11/2003 |
| WO | 2004/082528 A3 | 9/2004 |
| WO | 2006/036690 A1 | 4/2006 |
| WO | 2005/058408 A1 | 6/2006 |
| WO | 2006/083763 A1 | 8/2006 |
| WO | 2006/128193 A2 | 11/2006 |
| WO | 2007/051620 A1 | 5/2007 |
| WO | 2008/072838 A1 | 6/2008 |
| WO | 2008/097589 A1 | 8/2008 |
| WO | 2009/153768 A1 | 12/2009 |
| WO | 2011/143263 A2 | 11/2011 |
| WO | WO 2012/173995 A2 | 12/2012 |
| WO | WO 2013078497 A1 * | 6/2013 ........... A61F 2/2418 |
| WO | 2013/116785 A1 | 8/2013 |
| WO | WO 2014/110019 A1 | 7/2014 |
| WO | 2014/144020 A1 | 9/2014 |

\* cited by examiner

LOW-PROFILE PROSTHETIC VALVE STRUCTURE

RELATED APPLICATIONS

This application is a continuation of U.S. patent application Ser. No. 14/212,442, filed Mar. 14, 2014, now U.S. Pat. No. 9,486,314, entitled Low-Profile Prosthetic Valve Structure which is related to and claims priority benefit of U.S. Provisional Application Ser. No. 61/800,153 filed Mar. 15, 2013 entitled Low-Profile Prosthetic Valve Structure, all of which are hereby incorporated by reference herein in their entireties.

BACKGROUND OF THE INVENTION

Replacing heart valves with prosthetic valves was, until recently, a complicated surgical procedure that involved cutting open the chest, establishing blood flow through a blood pump, stopping the heart, etc. This complicated procedure, even when performed perfectly, required extensive recovery time due to the invasiveness and damage done to access the implantation site. Additionally, the risk of infection or other complications is extremely high.

Numerous advancements have been made to develop prosthetic valves that can be implanted percutaneously, using a catheter to snake the prosthetic valve through the vasculature to the implantation site. If successful, the recovery time is greatly minimized relative to conventional open-heart surgery.

A designer of a percutaneously-delivered prosthetic valve is faced with numerous challenges, however. First and foremost is designing a prosthetic valve that can be compressed enough to be inserted into a catheter small enough to be navigated to the valve site through the vasculature. Other challenges include anchoring the valve at the valve site so the valve does not migrate after release; including a support structure for the valve that is robust enough to push the native, often calcified valve out of the way and prevent it from later interfering with the function of the new valve; ensuring that the new valve allows proper flow in a desired direction and effectively stops flow in the opposite direction; ensuring that no blood flows around the sides of the implanted device (this is known as perivalvular leakage); designing a prosthetic valve device that does not fail due to fatigue after hundreds of thousands of cycles of leaflet function; designing a valve that meets all of these criteria and can still be manufactured economically; and the list goes on.

These prosthetic valves, and their respective delivery catheters, are designed to replace a particular native valve, such as the aortic valve, for example. Percutaneous navigation to a valve is easiest, and least traumatic to the patient, when a smaller catheter is used. Smaller catheters, however, present challenges when designing effective prosthetic valves that can be compressed enough to fit, and slide, within the lumen of a small catheter, such as a 16 Fr or even a 14 Fr catheter. Significant strides have been made in recent years in designing prosthetic valves that have reduced profiles when in a catheter-loaded configuration. For example, the devices described in U.S. Patent Publication Number 2006/0271166 to Thill et al., the contents of which are incorporated by reference herein, can assume an elongated, unfolded configuration when loaded into a catheter and, when released from the catheter at a target site, resume a folded configuration. The present invention is directed to taking this innovative concept and presenting additional ways that the loaded configuration could present an even lower profile.

OBJECTS AND SUMMARY OF THE INVENTION

One aspect of the invention is directed to a prosthetic valve device that presents a low profile in a catheter-loaded configuration.

Another aspect of the invention is directed to a prosthetic valve device that is sized to replace an aortic valve and capable of being delivered using a small, flexible catheter.

Another aspect of the invention is directed to a prosthetic valve device that comprises two components are connected but positioned in series (spaced apart axially) in a delivery catheter to reduce the size of the delivery catheter required.

One aspect of the invention provides a device for replacing a native valve comprising: a stent; a tissue sleeve; and, an anchoring mechanism usable to secure said tissue sleeve within said stent; wherein, in a configuration inside a delivery catheter, said anchoring mechanism is not located within said stent; and wherein, in a deployed configuration, said tissue sleeve is located within said stent.

Another aspect of the invention provides prosthetic valve device that comprises a braided anchoring mechanism connected at a proximal end to a wireform.

Another aspect of the invention provides an implantable device that includes a support structure having an extended configuration and a folded configuration, the support structure having a first end, a second end and a preformed fold between said first end and said second end, wherein said preformed fold at least assists in inverting said first portion into said second portion when said support structure is released from a delivery device, and a prosthetic valve structure including a hinged end hingedly attached to said support structure first end, thereby allowing said support structure first portion to invert into said support structure second portion without inverting said prosthetic valve structure.

Another aspect of the invention provides an implantable prosthetic valve structure with a support structure that has a folded configuration in which the prosthetic valve structure extends, at least partially, into said support structure.

Another aspect of the invention provide a prosthetic valve device that includes a support structure that has inwardly curved sidewalls when it is in a folded configuration.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
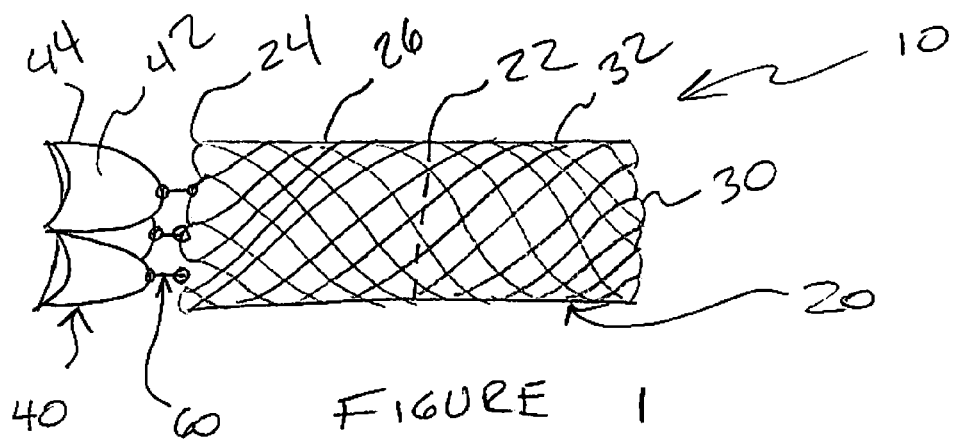
FIG. 1 is an elevation of an embodiment of the invention.

Specific embodiments of the invention will now be described with reference to the accompanying drawings.

This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring first to FIG. 1 there is shown a device 10 of the invention. Device 10 generally includes a support structure 20, a valve assembly 40, and a connection 60 between the support structure 20 and the valve assembly 40. FIG. 1 shows the device 10 in an elongate configuration prior to being compressed in order to fit within the lumen of a delivery catheter. It can be seen that the support structure 20, the valve assembly 40, and the connection mechanism 60 are all linearly arranged along a longitudinal axis in a series configuration, with no overlapping of components.

With regard to the support structure, a dotted line 22 represents a preformed fold created in the support structure 20 that at least partially causes the device 10 to fold inwardly on itself when released from a delivery catheter. The support structure 20 can be described as having a first end 24, a first portion 26 between the first end 24 and the preformed fold 22, a second end 30, and second portion 32 between the second end 30 and the preformed fold 22.

The valve assembly 40 includes tissue valve 42 attached to a wireform 40. The wireform 40 gives structural integrity to the tissue valve 44.

The connection 60 between the valve assembly 40 and the support structure 20 is described in more detail below.

Figure 2:
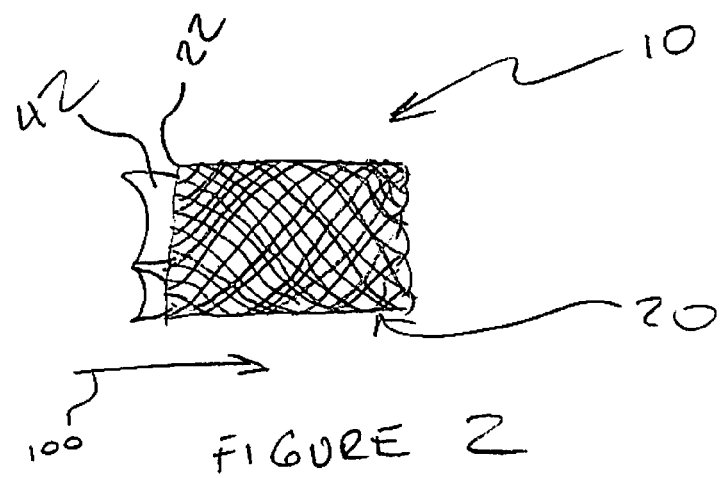
FIG. 2 is an elevation of an embodiment of the invention in a folded configuration.

FIG. 2 shows the device 10 of FIG. 1 in a fully expanded, delivered configuration. The device 10 has folded inwardly on itself such that the fold 22 is now defining the proximal end of the support structure 20. As the device 10 folded, the wireform 40, which contains a tissue valve 42, is drawn into the support structure 20. Because the first portion 26 is now inverted, in other words, it is inside-out in comparison to its prefolded configuration of FIG. 1, the connection mechanism 60 must hinge or pivot in order to maintain the orientation of the valve assembly 40. Because the connection mechanism 60 hinges, when the first portion 24 inverts into the second portion 32, the valve assembly 40 moves only linearly (axially) into the support structure 20, as shown by the arrow 100 in FIG. 2. Thus, only one preformed fold 22 is needed in the support structure 20 to allow the valve assembly 40 to maintain its orientation while moving axially.

Figure 3:
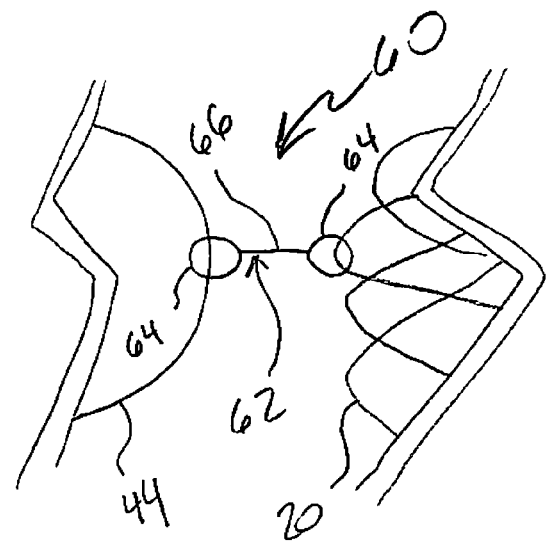
FIG. 3 is a partial view of an embodiment of the invention.

FIG. 3 shows an embodiment of a connection mechanism 60. The connection mechanism 60 may be a link 62 having two ring connectors 64 separated by a spacer 66. The spacer 66 is sized to ensure that, in the elongated configuration, the connection mechanism 60 adequately separates the support structure 20 from the valve assembly 40. The connection mechanism 60 may be constructed of a variety of biocompatible material such as an alloy, including but not limited to stainless steel and Nitinol, or may be a polymer or other suitable non-metallic material.

Figure 4:
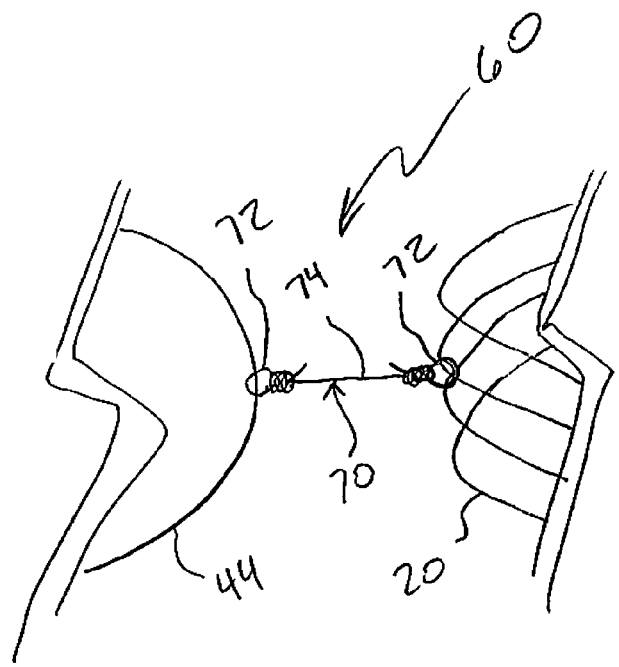
FIG. 4 is a partial view of an embodiment of the invention.

FIG. 4 shows another embodiment of a connection mechanism 60. This connection mechanism 60 may be a tether 70 having ends 72 that are tied to the wireform 44 of the valve assembly 40 and to the support structure 20. The tether may be constructed of any suture material or may be a wire having suitable flexibility to be tied in a knot. The length of the tether 70 between the tied ends 72 constitutes a spacer 74 that is sized to ensure adequate separation of the support structure 20 from the valve assembly 40 in the elongated configuration of FIG. 1.

Figure 5:
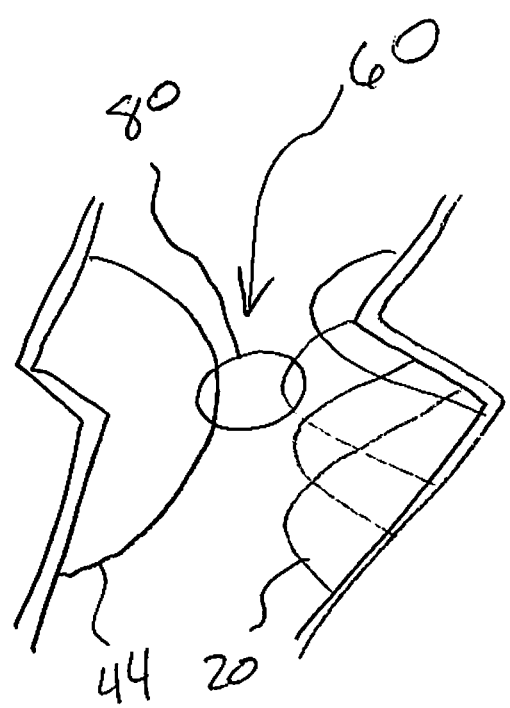
FIG. 5 is a partial view of an embodiment of the invention.

FIG. 5 shows an embodiment of a connection mechanism 60 that is a single loop 80. The loop 80 extends around the wireform 44 and a strand of the support structure 20. The loop 80 is sized to ensure adequate separation of the support structure 20 from the valve assembly 40 in the elongated configuration of FIG. 1.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An implantable device comprising:
   a support structure having a single preformed fold and an unfolded configuration and a folded configuration and including:
   a first end;
   a second end directed away from said first end; and,
   a lumen extending between said first end and said second end;
   wherein said support structure is biased toward a folded configuration in which said first end is inverted into said lumen, such that the first end and the second end are both oriented in a common direction;
   wherein said support structure tends to assume said folded configuration when said support structure is released from a delivery device;
   a prosthetic valve structure hingedly attached to said support structure first end such that said prosthetic valve structure is not inverted when said support structure inverts.

2. The implantable device of claim 1 wherein said hinged end is attached to said support structure first end with a connector.

3. The implantable device of claim 2 wherein said connector comprises a hinge.

4. The implantable device of claim 2 wherein said connector comprises a link.

5. The implantable device of claim 4 wherein said link comprises two ring connectors separated by a spacer.

6. The implantable device of claim 1 wherein, in said unfolded configuration, said connector separates said support structure from said valve assembly.

7. The implantable device of claim 1 wherein said connector comprises a tether.

8. An implantable device comprising:
   a support structure having a first end and a second end and a lumen therebetween, and a single preformed fold;
   a valve assembly;
   a connector connecting said valve assembly to said first end of said support structure;
   wherein said implantable device has a first configuration and a second configuration;
   wherein in said first configuration, said support structure is unfolded, said first end faces a first direction and said second end faces a second direction opposite said first direction, and said support structure, said valve assembly, and said connector are axially arranged;
   wherein in said second configuration, said single preformed fold is folded and said first end is inverted into said lumen such that said first end faces said second direction and said valve assembly is drawn at least partially into said lumen by said connector.

9. The implantable device of claim 8 wherein said connector pivots such that said when said support structure inverts, said valve assembly does not invert.

10. The implantable device of claim 8 wherein said connector comprises a hinge.

11. The implantable device of claim 8 wherein said connector comprises a link.

12. The implantable device of claim 11 wherein said link comprises two ring connectors separated by a spacer.

13. The implantable device of claim 8 wherein, in said first configuration, said connector separates said support structure from said valve assembly.

14. The implantable device of claim 8 wherein said connector comprises a tether.

15. The implantable device of claim 14 wherein said tether comprises a first end tied to the support structure and a second end tied to the valve assembly.

16. The implantable device of claim 8 wherein said connector comprises a loop.

17. A method of delivering an implantable device comprising:
arranging a first component, a connector, and a second component axially in a delivery catheter, said first component in an unfolded configuration but having a single preformed fold that is biased toward a folded configuration; said connector connecting said first component and said second component such that said first and second components do not overlap;
releasing said first component, said connector, and said second component at a target site from said catheter;
allowing said first component to assume said folded configuration such that opposite ends thereof face a common direction while said connector pivots, thereby drawing said second component axially toward said first component.

18. The method of claim 17 wherein releasing said first component, said connector, and said second component at a target site from said catheter comprises first releasing said first component followed by releasing said connector and said second component.

19. The method of claim 17 wherein arranging a first component, a connector and a second component axially in a delivery catheter comprises arranging a support structure, a connector, and a valve assembly in a delivery catheter.

20. The method of claim 17 wherein arranging a first component, a connector, and a second component axially in a delivery catheter, said first component in an unfolded configuration but biased toward a folded configuration; said connector connecting said first component and said second component such that said first and second components do not overlap, comprises arranging said first component, said connector, and said second component axially in said delivery catheter such that said first component and said second component are spaced apart from each other.

* * * * *